United States Patent [19]

Brightbill

[11] Patent Number: 5,149,330
[45] Date of Patent: Sep. 22, 1992

[54] CATHETER CONVERTIBLE FROM SINGLE TO MULTILUMEN

[75] Inventor: Jerry R. Brightbill, Framingham, Mass.

[73] Assignee: The Kendall Company

[21] Appl. No.: 639,623

[22] Filed: Jan. 10, 1991

[51] Int. Cl.⁵ ........................................... A61M 25/00
[52] U.S. Cl. ..................................... 604/280; 604/93; 604/264; 604/283
[58] Field of Search ...................... 604/53, 93, 96, 101, 604/264, 280, 282, 283, 43, 164, 165; 606/194; 128/656–658, 772

[56] References Cited

U.S. PATENT DOCUMENTS

| | | | |
|---|---|---|---|
| 3,771,527 | 11/1973 | Ruisi | 604/96 X |
| 3,863,632 | 2/1975 | Schwartz | 604/164 |
| 4,202,332 | 5/1980 | Tersteegen et al. | 604/164 |
| 4,318,402 | 3/1982 | Vaillancourt | 604/280 |
| 4,710,181 | 12/1987 | Fuqua | 604/280 |
| 4,819,664 | 4/1989 | Nazari | 604/96 X |
| 4,850,373 | 7/1989 | Zatloukal et al. | 128/749 |
| 4,935,017 | 6/1990 | Sylvanowicz | 604/280 |
| 4,976,691 | 12/1990 | Sahota | 604/96 |

Primary Examiner—C. Fred Rosenbaum
Assistant Examiner—C. Maglione
Attorney, Agent, or Firm—Alvin Isaacs

[57] ABSTRACT

A catheter capable of being converted from a single lumen catheter into a multilumen catheter. The catheter of the present invention comprises a first large bore catheter tube and a second catheter tube having at least one lumen and an outer diameter which is smaller than the inner diameter of the first catheter tube and which is capable of being disposed within the first catheter tube. When the second catheter tube is disposed within the first catheter tube, the second catheter tube abuts a portion of the inner wall of the first catheter tube to form a single lumen between the inner wall of the first catheter tube and the outer wall of second catheter tube. The first catheter tube has a first connector portion at its proximal end which is mateable with a second connector portion at the proximal end of the second catheter tube. The connector portions are mateable in fluid tight relationship and are operative to maintain the first and second catheter tubes in nested relationship to each other and provide multiple lumens.

21 Claims, 2 Drawing Sheets

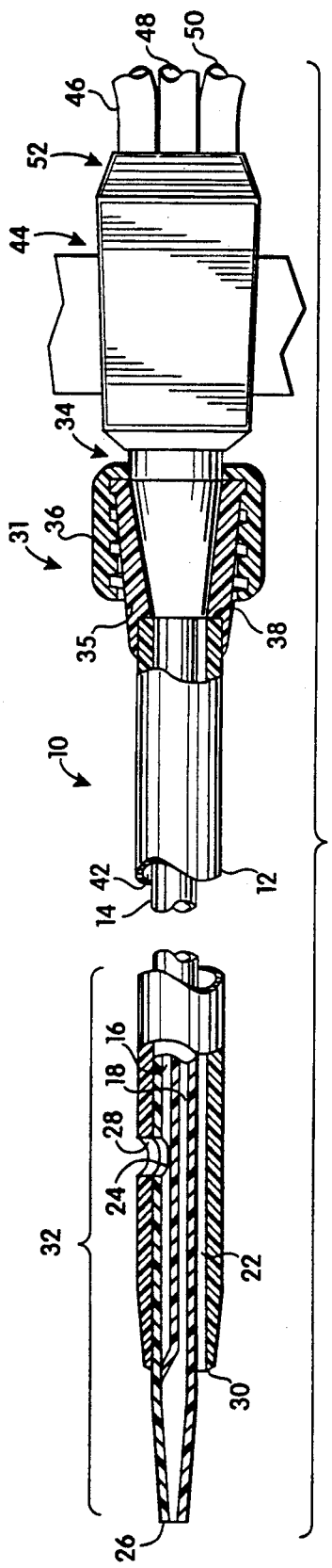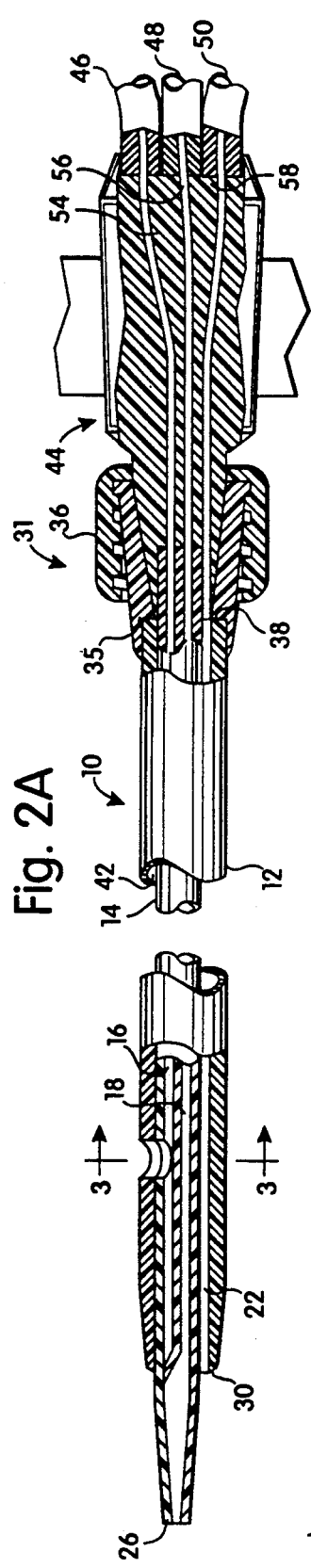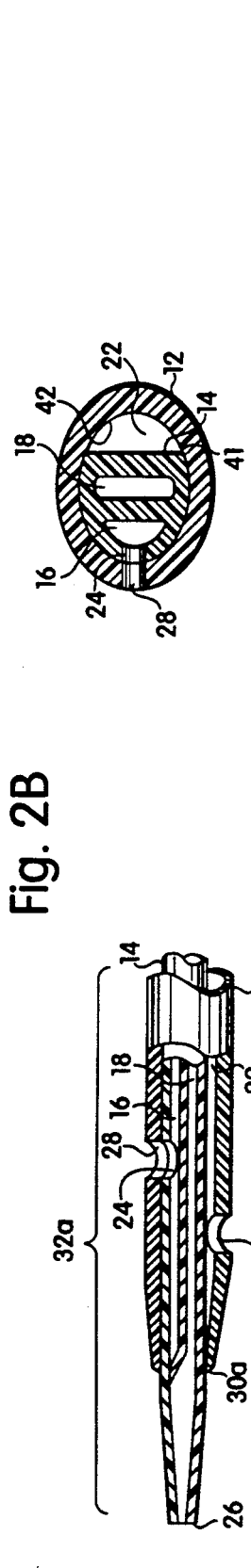
Fig. 2A
Fig. 2B
Fig. 3
Fig. 4

CATHETER CONVERTIBLE FROM SINGLE TO MULTILUMEN

FIELD OF THE INVENTION

The present invention relates to catheters and more particularly to convertible catheters for conversion from single to multiple lumens.

BACKGROUND OF THE INVENTION

During a surgical operation, doctors typically insert large bore venous catheters into the patient in order to introduce blood quickly and efficiently. Once the surgery is completed, and the patient is in post-op, it becomes necessary to remove the large bore venous catheter and replace it with a multilumen catheter. The multilumen catheter facilitates the simultaneous introduction of medication as well as blood into the patient, and may also function to simultaneously withdraw blood from the patient or monitor the patient's blood pressure.

There are several disadvantages associated with exchanging catheters as described above. The removal of a large bore catheter from the patient may cause profuse bleeding which must be controlled, and which makes difficult reinsertion of a multilumen catheter in the same general puncture site. Furthermore, the patient is subjected to increased discomfort and possible infection inherent with the insertion, removal and reinsertion of different catheters.

Therefore, it would be desirable to have a catheter which overcomes the above described disadvantages, which is economical to produce and which is compatible with existing medical equipment used with conventional multiple lumen catheters.

SUMMARY OF THE INVENTION

In accordance with the present invention, a catheter is provided which is capable of being converted from a large bore single lumen catheter into a multilumen catheter. The catheter of the present invention comprises a first, large bore catheter tube and a second catheter tube having at least one lumen and an outer diameter which is smaller than the inner diameter of the first catheter tube and which is capable of being disposed within the first catheter tube. When the second catheter tube is disposed within the first catheter tube, the second catheter tube abuts a portion of the inner wall of the first catheter tube to form a single lumen between the inner wall of the first catheter tube and the outer wall of the second catheter tube.

The first catheter tube has a first connector portion at its proximal end which is mateable with a second connector portion at the proximal end of the second catheter tube The connector portions are mateable in fluid tight relationship and are operative to maintain the first and second catheter tubes in nested relation to each other and provide multiple lumens.

A manifold is attached to or formed with the proximal end of the second catheter tube which facilitates fluid communication between extension tubing and the lumen or lumens of the second catheter tube. Furthermore, when the first and second catheter tubes are assembled together, the manifold also provides fluid communication between the single lumen of the first catheter tube and extension tubing via a channel.

The first catheter tube can function as a relatively large bore single lumen catheter when it is desired to introduce large amounts of blood quickly and efficiently into the patient. When the need arises for a multilumen catheter, the large bore catheter need not be removed and replaced with a multilumen catheter. Instead, the second catheter tube may simply be inserted into the large bore catheter and secured by the connector portions to form a multilumen catheter which functions similarly to conventional multilumen catheters.

DESCRIPTION OF THE DRAWING

This invention will be more fully understood from the following solely exemplary detailed description taken in conjunction with the accompanying drawings in which:

FIG. 2A is a view, partly in section, of the second, dual-lumen catheter tube disposed within the first, large bore catheter tube;

FIG. 2B is a view similar to that of FIG. 2A and showing the channels in the manifold communicating with the respective lumens of the first and second catheter tubes and the extension tubing;

FIG. 3 is a cross-sectional view taken along lines 3-3 of FIG. 2B; and

FIG. 4 is a view, partly in section, showing an alternative embodiment of the distal portion of the catheter shown in FIGS. 2A and 2B.

DETAILED DESCRIPTION OF THE INVENTION

Figure 1:
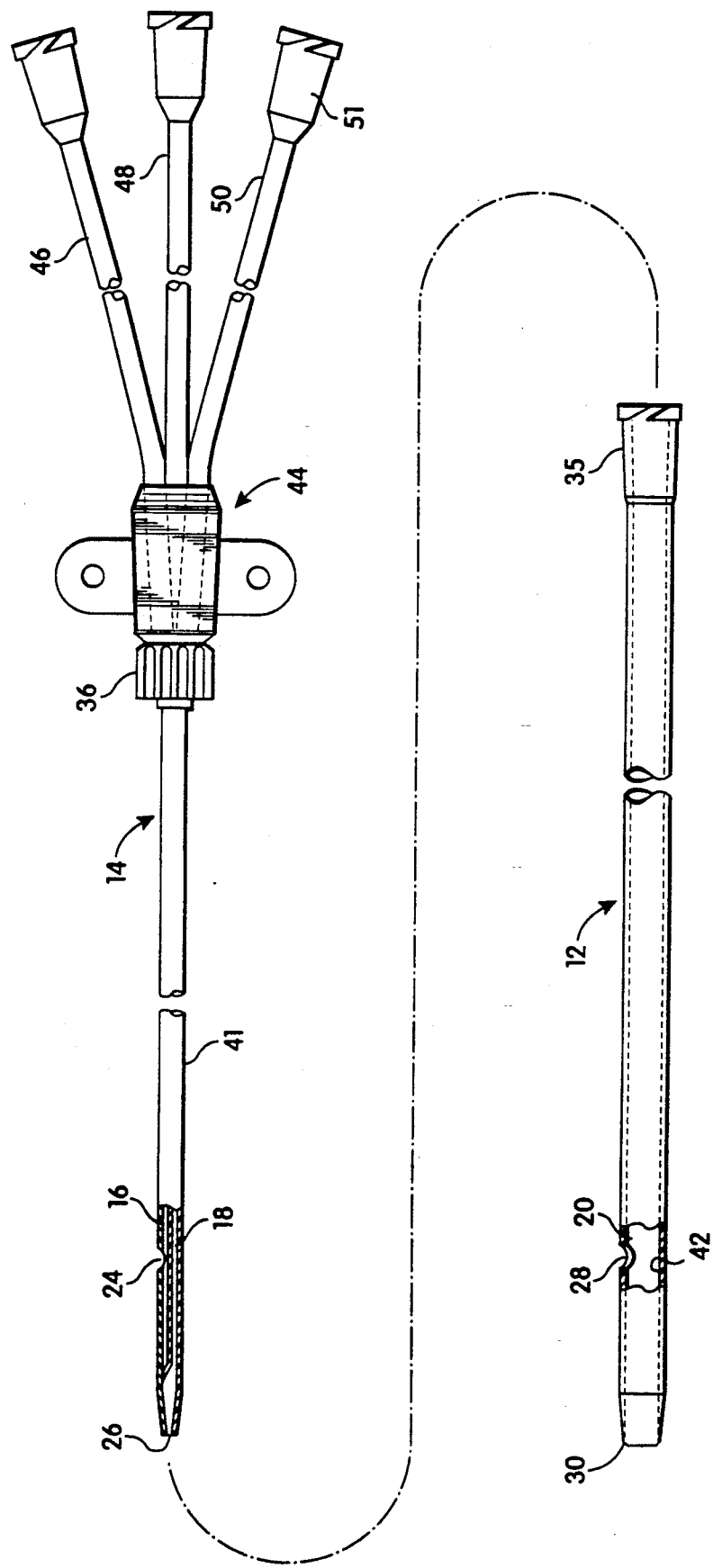
FIG. 1 is a view, partly in section, of the first, large bore catheter tube and the second, dual-lumen catheter tube prior to insertion within the first catheter tube.

Referring now to FIGS. 1-3, one embodiment of the conversion catheter in accordance with the present invention is shown. The convertible catheter 10 comprises a first flexible elongated large-bore catheter tube 12, e.g. 13 gauge or larger, and a second flexible elongated dual-lumen catheter tube 14.

The second catheter tube 14 has an outer diameter which is smaller than the inner diameter of the first catheter tube 12 and which may therefore be inserted into the first catheter tube 12 as shown in FIGS. 2A-2B. Typically the first catheter tube 12 will have an outer diameter of at least on the order of 0.092 inch. The second catheter tube 14 is also longer than first catheter tube 12 so as to extend longitudinally outward at both its distal and proximal ends from catheter tube 12 when the two catheter tubes are assembled together.

The second catheter tube 14 is a dual-lumen catheter tube defining first and second lumens 16 and 18. As seen in FIG. 3, lumens 16 and 18 are preferably of a shape other than circular to optimize the space within the second catheter tube. The first catheter tube 12 has a bore 20 which extends therethrough. When the second catheter tube 14 is inserted within the first catheter tube 12, a portion of the outer wall 41 of the second catheter tube 14 abuts a portion of the inner wall 42 of the first catheter tube 12, as seen in FIG. 3. A single lumen 22 is formed in the portion of the bore 20 between the inner wall 42 of the first catheter tube 12 and the outer wall 41 of the second catheter tube 14, thereby providing a triple lumen catheter. Lumen 18 may, for example, have an internal diameter of on the order of 0.047 inch, which is equivalent to a 16 gauge catheter, while lumens 16 and 22 may have an effective cross-sectional area of on the order of 0.033 inch, which is equivalent to an 18 gauge catheter.

It should be understood that the second catheter tube 14 may alternatively comprise only one lumen, thereby forming a dual-lumen catheter when inserted into the first catheter tube 12. Likewise, the second catheter tube 14 may comprise more than two lumens. However, for exemplary purposes, one embodiment of the present invention is shown having a second catheter tube 14 with two lumens and providing a single to triple lumen conversion.

The first lumen 16 of the second catheter tube 14 is shown to terminate in a side opening 24 upstream from the distal end 26 of the second catheter tube 14. The second lumen 18 of the second catheter tube 14 terminates coextensively with the distal end 26 of the second catheter tube. The first catheter tube 12 has a side opening 28 which becomes aligned with the side opening 24 of the second catheter tube 14 when the second catheter tube 14 is inserted and seated within the first catheter tube 12, thereby allowing fluid passage from the first lumen 16 of the second catheter tube 14 to the outside of the first catheter tube 12.

The single lumen 22, formed in the portion of the bore 20 of the first catheter tube 12 when the second catheter tube 14 is inserted within the first catheter tube 12, terminates coextensively with the distal end 30 of the first catheter tube 12.

When the first 12 and second 14 catheter tubes are assembled together to form the multiple lumen catheter, the lumens 16, 18, 22 are independent and noncommunicative with one another, and various fluids simultaneously carried thereby do not mix prior to entering the blood stream. Furthermore, as can be seen in FIGS. 2A-2B, each of the lumens 16, 18, 22 terminate at positions spaced apart from one another, thereby ensuring that fluids simultaneously carried within each of the lumens 16, 18, 22 do not mix prior to being assimilated into the bloodstream.

Suitable materials from which catheter tubes 12, 14 may be made include flexible, sterilizable, materials such as polyurethane, silicone, polyvinyl chloride (PVC) and nylon. Polyurethane is preferred. Furthermore, the second catheter tube 14 may be formed from a less rigid material such as a softer, more flexible polyurethane, thereby providing an overall softer distal end portion 32 of the catheter 10 when the second catheter tube 14 and first catheter tube 12 are assembled together.

A connector or coupler 31 provides fluid tight connection of the catheters 12 and 14 in nested relation. The connector 31 includes a first connector portion 35 attached to or formed with the proximal end of catheter 12, and a second connector portion 36 attached to or formed with the proximal end of catheter 14. The connector portions 35 and 36 are mateable when the second catheter tube 14 is inserted within the first catheter tube 12. When the connector portions are mated, the second catheter tube 14 extends along the bore 20 of the first catheter tube 12 a position such that the second catheter tube 14 abuts a portion of the inner wall 42 of the first catheter tube 12, and the side opening 24 of the second catheter tube 14 abuts and is aligned with the side opening 28 of the first catheter tube 12, as shown in FIG. 3. To insure or facilitate proper alignment, side opening 24 may be slightly larger than side opening 28.

The connector portions 35, 36 may respectively be the male and female assemblies of a standard luer connector with locking threads, and may be made from rigid, sterilizable, plastic materials such as polyurethane, polycarbonate, PVC, etc. The connector 31 may also be of other mateable configuration which provides fluid tight coupling. The connecting portions 35 and 36 may be secured to the respective first 12 and second 14 catheter tubes by known means such as adhesive or heat sealing. Alternatively, the connector portions may be integrally formed, such as by insert-molding, with the respective catheter tubes.

A manifold 44 is secured to the proximal end 34 of the second catheter tube 14. Extension tubing 46, 48, 50 has end portions encapsulated within the manifold and extends outwardly from the manifold, terminating in couplings 51 of known type such as luer fittings for connection to fluid transfer devices or pressure monitoring devices as is known in the art. The extension tubing may be made from any suitable medical grade tubing material.

The manifold 44 provides fluid communication between the lumens 16 and 18 of the second catheter tube 14 and extension tubing 46 and 48 via respective channels 54 and 56. When the second catheter tube 14 is inserted within the first catheter tube 12, and the connector portions 35 and 36 are mated, the manifold 44 also provides fluid communication between the single lumen 22 of the first catheter tube 12 and extension tubing 50 via a channel 58.

The manifold 44 may be formed from a rigid, sterilizable, plastic material which can be molded or otherwise formed using known techniques. Such materials include polycarbonate, polyurethane, and PVC. The manifold 44 may be separately formed and then sealed to the proximal end 34 of the second catheter tube 14. Alternatively, the manifold 44 may be formed integrally with the second catheter tube 14.

Referring now to FIG. 4, an alternate embodiment of the distal portion 32a of the catheter 10 is shown. In this embodiment, the distal end 30a of the first catheter tube 12 is tapered and abuts the outer wall of the second catheter tube 14 which outwardly extends beyond the distal end 30a of the first catheter tube 12. The single lumen 22 of the first catheter tube 12 terminates in a side opening 60 upstream from the tapered distal end 30a of the first catheter tube 12 and downstream from side openings 24, 28. Alternatively, the positions of the side openings may be reversed so that side opening 60 is downstream from side openings 24, 28. The side opening 60 in the first catheter tube 12 enables lumen 22 to aspirate fluids from the patient as well as deliver fluids to the patient.

The manner of using the catheter of the present invention is substantially the same as using a conventional single lumen or multilumen catheter. The first catheter tube 12 may be coupled to a fluid transfer device for the delivery of blood to the patient via extension tubing having a connector portion capable of mating with the connecting portion 35 of the first catheter tube 12. When it is necessary that a multilumen catheter be used, extension tubing connected to the first catheter tube 12 is removed and the second catheter tube 14 is inserted into the first catheter tube 12. The mateable connector portions are secured together to form a fluid tight seal. Thereafter, the extension tubing 46, 48, 50 extending outwardly from the manifold 44 is connected to fluid transfer devices or pressure monitoring devices as are well known in the art. Once the first 12 and second 14 catheter tubes are assembled together, the catheter functions substantially the same as a conventional multilumen catheter.

This invention is not to be limited by what has been particularly shown and described, except as indicated by the appended claims.

What is claimed is:

1. A venous catheter capable of being converted from a single lumen large bore venous catheter into a multilumen catheter comprising:

a first flexible elongated large bore catheter tube adapted for insertion in the vein of a patient and having a proximal end, a distal end, an inner wall and a single bore extending there through;

a second flexible elongated catheter tube having a proximal end, a distal end, an outer wall and defining at least one lumen extending there through and terminating in at least one opening; said second catheter tube having an outer diameter which is smaller than the inner diameter of said first catheter tube, and capable of being removably disposed within said first catheter tube abutting a portion of the inner wall of said first catheter tube and defining a single lumen in the portion of the bore between the inner wall of said first catheter tube and the outer wall of said second catheter tube;

said single lumen terminating in at least one opening in said first catheter tube;

a connector having a first connector portion affixed to the proximal end of the first catheter tube, and a second connector portion affixed to the proximal end of the second catheter tube, said connector portions being mateable to provide a fluid tight coupling, said connector being a standard luer connector with locking threads;

said second catheter tube being removably coupled in a fluid tight relationship to said first catheter tube via said mateable connector portions.

2. The catheter of claim 1 wherein said second catheter tube further comprises a manifold coupled to said proximal end of said second catheter tube, and extension tubing coupled to said manifold;

said manifold providing separate fluid communication between said at least one lumen of said second catheter tube and said extension tubing via at least one channel, and wherein said manifold also provides fluid communication between said single lumen and said extension tubing via a channel when said first and second catheter tubes are assembled together in said fluid-tight relationship.

3. The catheter of claim 2 wherein said extension tubing is configured for attachment to fluid transfer devices or pressure monitoring devices.

4. The catheter of claim 2 wherein said manifold is integrally formed with said second catheter tube.

5. The catheter of claim 2 wherein said manifold extends proximally beyond said first and second catheter tubes when said second catheter tube is disposed within said first catheter tube and said respective mateable connector portions of said first and second catheter tubes are joined in said fluid tight relationship.

6. The catheter of claim 2 wherein said manifold is made from materials selected from the group consisting of polycarbonate, polyurethane, and PVC.

7. The catheter of claim 1 wherein said first connector portion of said first catheter tube is integrally formed with said first catheter tube.

8. The catheter of claim 1 wherein said second connector portion of said second catheter tube is integrally formed with said second catheter tube.

9. The catheter of claim 1 wherein said second catheter tube extends longitudinally outward from said distal end of said first catheter tube when said second catheter tube is disposed within said first catheter tube.

10. The catheter of claim 1 wherein said second catheter tube has one lumen.

11. The catheter of claim 10 wherein said one lumen terminates in at least one opening in said second catheter tube.

12. The catheter of claim 1 wherein said second catheter tube is a dual-lumen catheter having first and second lumens.

13. The catheter of claim 12 wherein said first lumen of said second catheter tube terminates in a side-opening in said second catheter tube upstream from said distal end of said second catheter tube, and said second lumen terminates coextensively with said distal end of said second catheter tube.

14. The catheter of claim 13 wherein said first catheter tube has a side opening which is in fluid tight alignment with said side opening in said second catheter tube when said second catheter tube is disposed within said first catheter tube, and said first and second mateable connector portions are joined in said fluid tight relationship.

15. The catheter of claim 14 wherein said single lumen of said first catheter tube terminates coextensively with said distal end of said first catheter tube.

16. The catheter of claim 14 wherein said distal end of said first catheter tube is tapered and abuts the second catheter tube, and wherein said single lumen terminates in a side-opening upstream from tapered distal end of said first catheter tube.

17. The catheter of claim 15 or 16 wherein said first and second lumens of said second catheter tube and said single lumen of said first catheter tube terminate at positions spaced apart from one another.

18. The catheter of claim 1 wherein said first and second catheter tubes are made from flexible, sterilizable materials.

19. The catheter of claim 18 wherein said materials are selected from the group consisting of polyurethane, silicone, polyvinyl chloride (PVC) and nylon.

20. The catheter of claim 19 wherein said first and second catheter tubes are made from polyurethane.

21. The catheter of claim 1 wherein said first and second connector portions are made from rigid, sterilizable, plastic materials.

* * * * *